(12) United States Patent
Richard et al.

(10) Patent No.: US 8,729,015 B2
(45) Date of Patent: May 20, 2014

(54) SOLID LIPID MICROCAPSULES CONTAINING GROWTH HORMONE INNER CORE MICROPARTICLES

(75) Inventors: Joel Richard, Mère (FR); Helen Baldascini, Rome (IT); Rita Agostinetto, Rocca Di Papa (IT); Luisa De Angelis, Folignano (IT); Frantz Deschamps, Nancy (FR)

(73) Assignee: Merck Patent GmbH, Darmstadt (DE)

( * ) Notice: Subject to any disclaimer, the term of this patent is extended or adjusted under 35 U.S.C. 154(b) by 519 days.

(21) Appl. No.: 12/809,397

(22) PCT Filed: Nov. 21, 2008

(86) PCT No.: PCT/EP2008/009849
§ 371 (c)(1),
(2), (4) Date: Jun. 18, 2010

(87) PCT Pub. No.: WO2009/080164
PCT Pub. Date: Jul. 2, 2009

(65) Prior Publication Data
US 2010/0310649 A1 Dec. 9, 2010

(30) Foreign Application Priority Data
Dec. 21, 2007 (EP) .................................... 07024906

(51) Int. Cl.
*A61K 38/27* (2006.01)
*A61K 9/16* (2006.01)
*C12M 1/02* (2006.01)
*C12M 3/04* (2006.01)

(52) U.S. Cl.
USPC ............ 514/5.1; 424/491; 424/43; 435/286.6

(58) Field of Classification Search
None
See application file for complete search history.

(56) References Cited

U.S. PATENT DOCUMENTS

| | | | |
|---|---|---|---|
| 5,219,572 A * | 6/1993 | Sivaramakrishnan et al. | 424/438 |
| 6,544,646 B2 * | 4/2003 | Vaghefi et al. | 428/402.24 |
| 6,967,028 B2 * | 11/2005 | Dulieu et al. | 424/501 |
| 2001/0044026 A1 | 11/2001 | Vaghefi et al. | |
| 2004/0115259 A1 * | 6/2004 | Bordes et al. | 424/465 |
| 2006/0088595 A1 * | 4/2006 | Asakawa et al. | 424/468 |
| 2010/0173002 A1 * | 7/2010 | Yulai et al. | 424/492 |

FOREIGN PATENT DOCUMENTS

| | | | | |
|---|---|---|---|---|
| JP | 60068044 | * | 4/1985 | .............. A61K 9/50 |
| WO | PCTEP0809849 | R | 5/2009 | |

* cited by examiner

Primary Examiner — Elly-Gerald Stoica
(74) Attorney, Agent, or Firm — Millen, White, Zelano, Branigan, P.C.

(57) ABSTRACT

The invention relates to growth hormone (GH) formulations having sustained-release properties, in particular human growth hormone (hGH) and methods for their preparation. The growth hormone formulations can be manufactured without denaturing of the protein and can conveniently be administrated to the person in need thereof by using a conventional syringe via a needle having a small diameter.

27 Claims, 7 Drawing Sheets

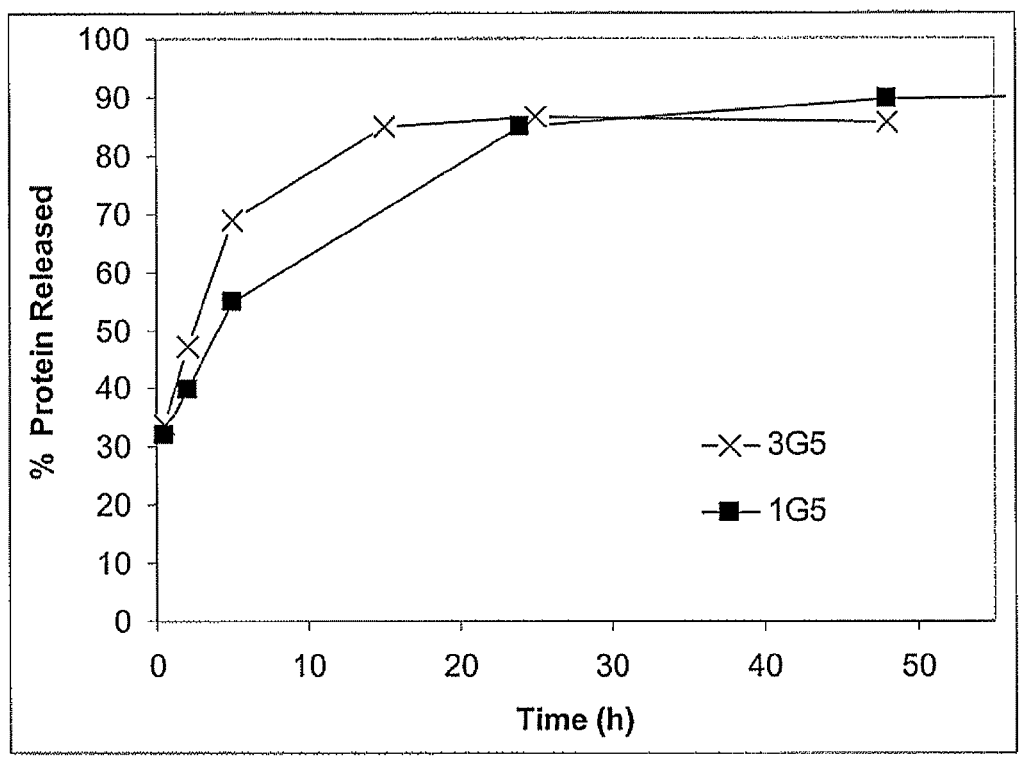
Figure 2a : In vitro release profiles for 2 Gelucire®-based microcapsule formulations (1G5, 3G5), containing 5 % hGH core microparticles. The % protein released is calculated based on the experimentally determined hGH loading of the microcapsules.

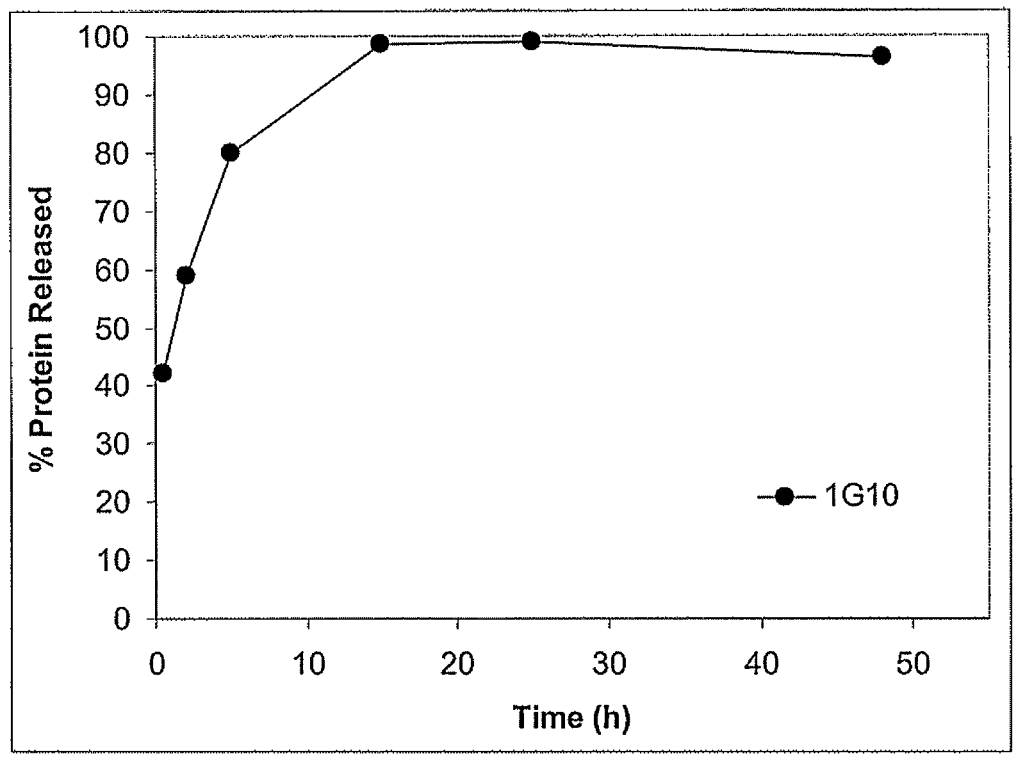
Figure 2b : In vitro release profiles for a Gelucire®-based microcapsule formulation with 10% payload hGH microparticles. The release profile is shown calculated with respect to the experimentally determined hGH loading

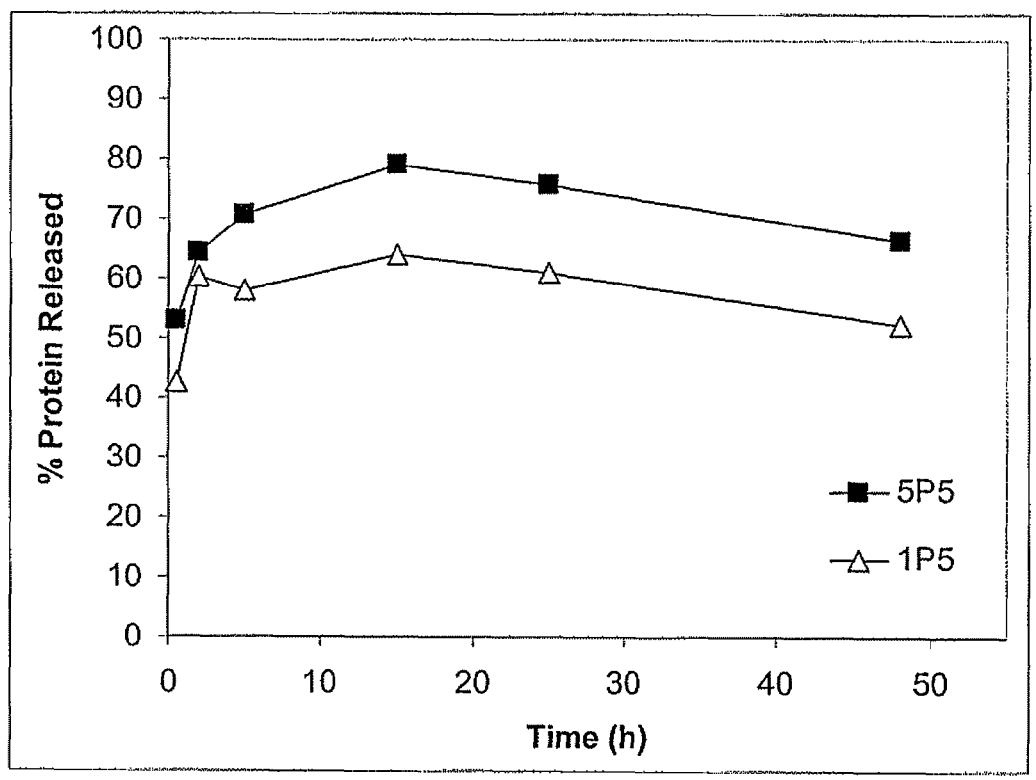
Figure 3 : In vitro release profiles for 2 Precirol®-based microcapsule formulations (1P5, 5P5). The % protein released is calculated based on the experimentally determined hGH loading of the microparticles.

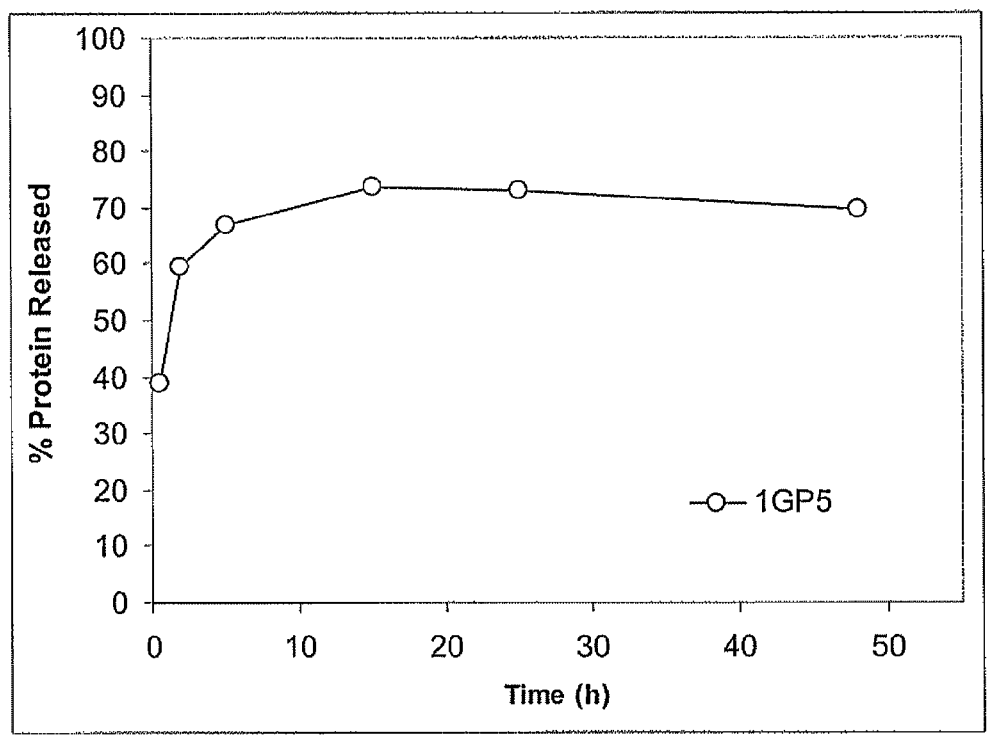
Figure 4 : In vitro release profiles for one Precirol®/Gelucire®-based formulation (1GP5). The % protein released is calculated based on the experimentally determined hGH loading of the microparticles.

```
FPTIPLSRLF  DNAMLRAHRL  HQLAFDTYQE  FEEAYIPKEQ  KYSFLQNPQT  SLCFSESIPT
60
PSNREETQQK  SNLELLRISL  LLIQSWLEPV  QFLRSVFANS  LVYGASDSNV  YDLLKDLEEG
120
IQTLMGRLED  GSPRTGQIFK  QTYSKFDTNS  HNDDALLKNY  GLLYCFRKDM  DKVETFLRIV
180
QCRSVEGSCG  F
```

Fig. 5: Amino acid sequence of human growth hormone

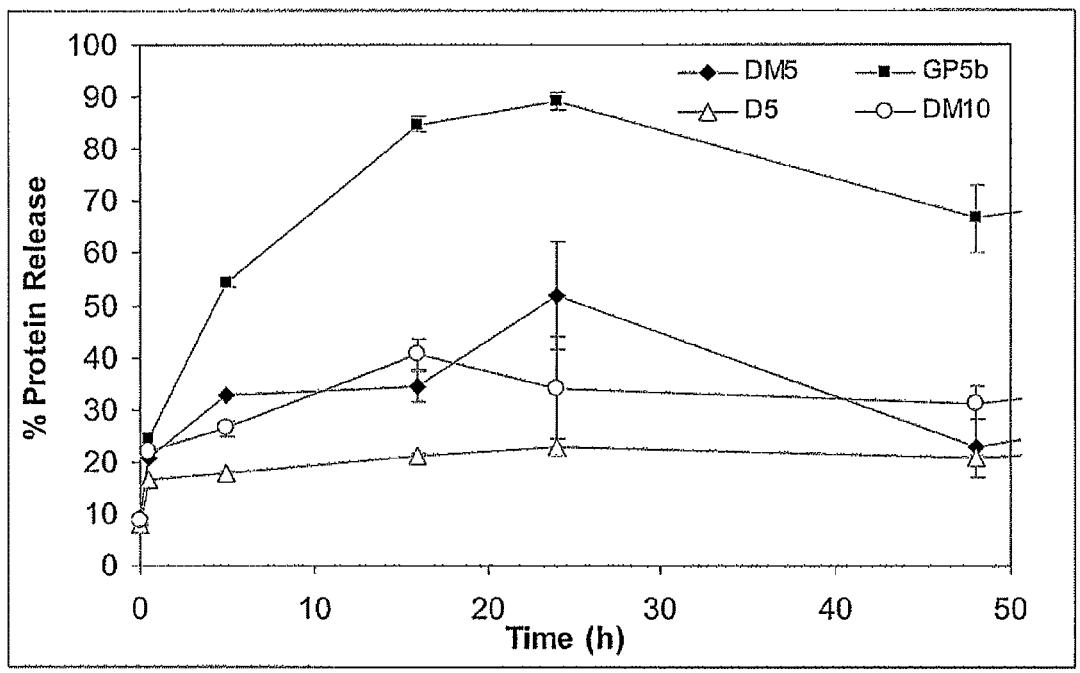
Figure 6 : In vitro release profiles for microcapsule formulations (DM5, GP5b, D5, DM10). The % protein released is calculated based on the experimentally determined hGH loading of the microparticles.

SOLID LIPID MICROCAPSULES CONTAINING GROWTH HORMONE INNER CORE MICROPARTICLES

This application is a National Stage entry of PCT/EP2008/009849 filed on Nov. 21, 2008.

The present invention relates to growth hormone (GH) formulations having sustained-release properties, in particular human growth hormone (hGH) and methods for their preparation. The growth hormone formulations can be manufactured without denaturing of the protein and can conveniently be administered to the person in need thereof by using a conventional syringe, or a mechanical or electronic injection device, via a needle having a small diameter. Current treatment regimens for hGH deficiency in humans are, for example, primarily based on hGH-delivery by subcutaneous injection. hGH plays a critical role in the regulation of cell and organ growth and in physiological function during various stages of development and aging. For example, overproduction of hGH results in gigantism in children and acromegaly in adults, whereas under-production leads to dwarfism in children [Mauras et al., J. Clin. Endocrinology and Metabolism, 85(10), 3653-3660 (2000); Frindik et al., Hormone Research, 51(1), 15-19 (1999); Leger et al., J. Clin. Endocrinology and Metabolism, 83(10), 3512-3516 (1998)], Turner's Syndrome (females only) [Bramswig, Endocrine, 15(1), 5-13 (2001); Pasquino et al., Hormone Research, 46(6), 269-272 (1996)] and chronic renal insufficiency [Carroll et al., Trends in Endocrinology and Metabolism, 11(6), 231-238 (2000); Ueland et al., J. Clin. Endocrinology and Metabolism, 87(6), 2760-2763 (2002); Simpson et al., Growth Hormone & IGF Research, 12, 1-33 (2002)]. In adults, hGH deficiency can affect metabolic processing of proteins, carbohydrates, lipids, minerals and connective tissue and can result in muscle, bone or skin atrophy [Mehls and Haas, Growth Hormone & IGF Research, Supplement B, S31-S37 (2000); Fine et al., J. Pediatrics, 136(3), 376-382 (2000); Motoyama et al., Clin. Exp. Nephrology, 2(2), 162-165 (1998)]. Other hGH deficiency-related disorders characterized by growth failure or problems include AIDS wasting syndrome [Hirschfeld, Hormone Research, 46, 215-221 (1996); Tritos et al., Am. J. Medicine, 105(1), 44-57 (1998); Mulligan et al., J. Parenteral and Enteral Nutrition, 23(6), S202-S209 (1999); Torres and Cadman, BioDrugs, 14(2), 83-91 (2000)] and Prader-Willi syndrome [Ritzen, Hormone Research, 56(5-6), 208 (2002); Eiholzer et al., Eur. J. Pediatrics, 157(5), 368-377 (1998)].

A number of products have been developed in an attempt to address the need for hGH therapeutics that are stable and long-acting and that, therefore, can be delivered by a less-frequent injection schedule.

To that end, various drug delivery technologies, such as hydrogels [Katakam et al., J. Controlled Release, 49(1), 21-26 (1997); Kim and Park, J. Controlled Release, 80(1-3), 69-77 (2002)], liposomes [Weiner et al., J. Pharm. Sci., 74(9), 922-925 (1985)], oil emulsions [Yu et al., J. Pharm. Sci., 85(4), 396-401 (1996); Zhao et al., J. Dairy Sci., 75(11), 3122-3130 (1992)] and biodegradable polymer microspheres [Jostel et al., Clin. Endocrinol. (Oxf), 62 (5):623-627 (2005); Sun et al., J. Pharmacol. Exp. Ther., 289 (3):1523-1532 (1999); Jones et al., Adv. Drug Deliv. Rev., 28(1): 1-84 (1997); Johnson et al., Wat Med, 2(7):795-799 (1996)], have been employed. However, the resulting hGH formulations often display an undesirable burst release of the drug or may be difficult to manufacture.

For example, NUTROPIN DEPOT®, is an injectable suspension of recombinant human growth hormone (r-hGH)-containing polylactide-co-glycolide (PLG) microspheres (see http://www.gene.com). Significant manufacturing costs have led to withdrawal of that product from the market. Moreover, studies involving the administration of NUTROPIN DEPOT®, in pediatric patients lead to adverse injection-site reactions, resulting in nodules, erythema, pain, bruising, itching, lipoatrophy and puffiness.

Another product currently in development by LG Pharmaceuticals Inc. (South Korea), is a microparticle suspension formulation containing hGH, hyaluronate, lecithin, and triglyceride. Drawbacks of this product include unfavorable delivery means, specifically, a delivery fluid that must be injected by means of a 26 gauge needle [Kim et al., J. Controlled Release, 104: 323-335 (2005); U.S. Application No. 2005/0100605; EP 0918535 B1].

PCT patent applications WO 2004/060310 and WO 20041060920 refer to hGH formulations, including those comprising crystals of hGH complexed with polyelectrolytes (i.e., polycations). Such compositions are stable and capable of sustained hGH release for up to a period of 1 week. While the polycation-complexed hGH crystal components render these compositions stable and long-acting, there is the possibility that in some patients, the charged nature of the complexed crystal surface may lead to a local reaction, which includes mild redness and swelling at the injection site.

It is the object of the present invention to provide a sustained-release formulation, which largely avoids the disadvantages of the prior art formulations such as burst effects, limited sustained release properties and which does not contain auxiliaries causing adverse reactions such as polyelectrolytes. Further, the sustained release formulation should be easily administrable through a 27-29 gauge (G) needle by using a conventional syringe, or through a mechanical or electronic injection device.

Surprisingly it has been found that such a formulation can be obtained by providing microcapsules, which comprise at least one inner solid core containing a growth hormone, a bulking agent and a surfactant, and an outer shell surrounding such inner solid core comprising at least one lipid.

Accordingly, the present invention is directed to a particulate formulation comprising (1) at least one inner solid core containing at least a growth hormone, a bulking agent and a surfactant and (2) an outer shell comprising at least one lipid. The inner solid core is made of at least one microparticle containing a growth hormone. Microcapsules with solid multi-cores, i.e. containing more than one growth hormone microparticles surrounded by the outer shell, are also part of the invention.

Growth hormone that can be formulated in accordance with the present invention may be from animal origin, such as bovine or porcine growth hormone. Preferably, it is from human origin. One preferred embodiment of the invention is directed to microcapsules, wherein the growth hormone is human growth hormone (hGH) or a functional derivative, fragment, variant, analogue, or a salt thereof which retains the biological activity of human growth hormone.

The term "human growth hormone", or "hGH", as used in the present invention, preferably comprises an amino acid sequence as depicted in FIG. 5. The term "human growth hormone" or "hGH" as used herein is also intended to include the naturally-occurring and synthetic derivatives, as noted above, including, without limitation, both the 20 kD and the 22 kD human growth hormone, GH-V, sulfoxidized and deamidated forms of GH, and other members of the growth hormone gene locus.

20 kD-hGH has been reported to occur in the pituitary as well as in the bloodstream (Lewis et al, J. Biol. Chem. 253: 2679 (1978); Lewis et al, Biochem. Biophys. Res. Comm.

92:511 (1980). This compound, which lacks the 15 amino acid residues from Glu-32 to Gln-46, arises from an alternative splicing of the messenger ribonucleic acid (DeNoto et al, Nucleic Acids. Res. 9:3719 (1981)). 20-K-hGH is made in the pituitary and secreted into the blood. It makes up about 5% of growth hormone output of adults, and about 20% of growth hormone output of children. It has the same growth promoting activity as 22 kD growth hormone, and has been reported to have equal to or greater than the amount of lipolytic activity as the 22 kD form. It binds to growth hormone receptors with equal affinity as the 22 kD growth hormone, and has one tenth the lactogenic (prolactin-like) bioactivity as the 22 kD hormone. Unlike 22 kD, the 20-k-hGH has weak anti-insulin activity.

GH-V is a variant of growth hormone found in the placenta. Further known derivatives of GH include deamidated and sulfoxidized forms of hGH.

Asparagine and glutamine residues in proteins are susceptible to deamidation reactions under appropriate conditions. Pituitary hGH has been shown to undergo this type of reaction, resulting in conversion of Asn-152 to aspartic acid and also, to a lesser extent, conversion of Gln-137 to glutamic acid (Lewis et al, Endocrinology 104:1256 (1979). Deamidated hGH has been shown to have an altered susceptibility to proteolysis with the enzyme subtilisin, suggesting that deamidation may have physiological significance in directing proteolytic cleavage of hGH.

Biosynthetic hGH is known to degrade under certain storage conditions, resulting in deamidation at a different asparagine (Asn-149). This is the primary site of deamidation, but deamidation at Asn-152 is also seen (Becker et al, 1988).

Both pituitary-derived and biosynthetic hGH undergo sulfoxidations at Met-14 and Met-125 (Becker et al, 1988). Oxidation at Met-170 has also been reported in pituitary but not biosynthetic hGH.

Both desamide hGH and Met-14 sulfoxide hGH have been found to exhibit full biological activity (Becker et al, Biotechnol. Appl. Biochem. 10:326 (1988). In accordance with the present invention, the hGH may be naturally-occurring human growth hormone, e.g. purified from the pituitary gland or blood or serum, or it may be recombinant hGH. Recombinant GH may be expressed in any suitable host, either a prokaryotic, or a eukaryotic host. E. coli is a host particularly suitable for expression of hGH, for instance. Preferably, hGH expressed in E. coli comprises an additional N-terminal methionine with respect to the human sequence, such hGH is also called Met-GH. Yeast, insect, or mammalian cells are further suitable for expression of recombinant growth hormone. The hGH may be expressed in human or animal cells, e.g. in Chinese Hamster Ovary (CHO) cells. Preferably, hGH may be expressed in murine cell lines such as e.g. the C127 cell line.

The term "growth hormone", as used herein, also includes functional derivatives, fragments, variants, or analogs of hGH having an amino acid sequence as depicted in FIG. 5, provided that the functional derivative, fragment, variant or analog retains the biological activity of growth hormone, i.e., acting as agonists to the growth hormone receptor. In other words, they are capable of binding to the growth hormone receptor to initiate the signaling activity of the receptor.

The term "functional derivatives", or "chemical derivatives", as used herein covers derivatives which may be prepared from the functional groups which occur as side chains on the residues of the N- or C-terminal groups, by means known in the art, and are included in the invention as long as they remain pharmaceutically acceptable, and do not significantly reduce the biological activity of hGH as described herein, i.e., the ability to bind the hGH receptor and initiate receptor signaling, and do not confer toxic properties on compositions containing it. Derivatives may have chemical moieties, such as carbohydrate or phosphate residues, provided such a derivative substantially retains the biological activity of hGH and remains pharmaceutically acceptable.

For example, derivatives may include aliphatic esters of the carboxyl groups, amids of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include, for example, polyethylene glycol side-chains, which may mask antigenic sites and extend the residence of the molecule in body fluids.

A growth hormone that has been derivatized or combined with a complexing agent may be long lasting. Therefore, an embodiment of the invention relates to PEGylated versions of human growth hormone. Such PEGylated versions of human growth hormone are e.g. described in WO 2005/074546. Growth hormones genetically engineered to exhibit long lasting activity in the body, are also examples for hGH derivatives within the scope of the present invention. hGH that is acetylated at the N-terminus has been isolated and identified (Lewis et al, 1979). It is not clear if acylation serves a regulatory role or is simply an artifact of the purification. However, it is expected that this molecule exhibits GH activity in a similar fashion to other hGH derivatives. Therefore, in an embodiment, the invention relates to a derivative of human growth hormone which is acetlyated at its N-terminus. One embodiment of the formulation according to the invention comprises a dimer of human growth hormone selected from the group consisting of a disulfide dimer connected through interchain disulfide bonds, a covalent irreversible non-disulfide dimer, a non-covalent dimer, and mixtures thereof.

As used herein the term "muteins" refers to analogs of an GH, in which one or more of the amino acid residues of a natural GH are replaced by different amino acid residues, or are deleted, or one or more amino acid residues are added to the natural sequence of an GH, without reducing considerably the activity of the resulting products as compared with the wild type GH. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes a GH under stringent conditions. A polynucleotide encoding hGH is a polynucleotide encoding a protein having the amino acid sequence depicted in FIG. 5.

The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated. Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al, Nucleic Acids Res, 12, 387-395, 1984), for example the programs BESTFIT and GAP, may be used to determine the % identity between two polynucleotides and the % identity and the % homology between two polypeptide sequences. BESTFIT uses the "local homology" algorithm of Smith and Waterman (Smith and Waterman J Mol Biol, 147,195-197, 1981, Advances in Applied Mathematics, 2, 482-489, 1981) and finds the best single region of similarity between two sequences. Other programs for determining identity and/or similarity between sequences are also known in the art, for instance the BLAST family of programs (Altschul S F et al, J Mol Biol, 215, 403-410, 1990, Altschul S F et al, Nucleic Acids Res., 25:38-3402, 19) and FASTA (Pearson W R and Lipman D J, Proc Nat Acad Sci USA, 85, 2444-2448, 1988).

1. Any such mutein preferably has a sequence of amino acids sufficiently duplicative of that of an GH (e.g. the amino acid sequence depicted in FIG. 5), such as to have substantially similar activity to GH. One activity of GH is its capability of binding the GH receptor. As long as the mutein has substantial binding activity to the GH receptor (OUR), it can be considered to have substantially similar activity to GH. Thus, it can be determined whether any given mutein has substantially the same activity as GH by means of routine experimentation comprising subjecting such a mutein, e.g., to a simple sandwich competition assay to determine whether or not it binds to an appropriately labeled GHR or cells expression GHR, such as radioimmunoassay or ELISA assay.

2. In a preferred embodiment, any such mutein has at least 60% or 70% or 80% or 90% or 95% or 98% or 99% identity or homology with the amino acid or DNA sequence of a GH. The amino acid sequence of hGH is shown in FIG. 5. DNA sequences encoding GH are known in the art, e.g. from DeNoto et al, 1981 or Martial et al., 1979.

3. Preferred changes for muteins in accordance with the present invention are what are known as "conservative" substitutions. Conservative amino acid substitutions of GH polypeptides, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, under 20, and preferably under ten, and do not remove or displace amino acids which are critical to a functional conformation, e.g., cysteine residues. Proteins and muteins produced by such deletions and/or insertions come within the purview of the present invention.

4. The term "fused protein" refers to a polypeptide comprising GH, or a mutein or fragment thereof, fused with another protein, which, e.g., has an extended residence time in body fluids. The fusion may be direct or via a linker, such as e.g. a peptide linker of 5 to 10 amino acids. GH may thus be fused to another protein, polypeptide or the like, e.g., an immunoglobulin or a fragment thereof. Fe portions of IgGs, such as IgG1, IgG2, IgG3 or IgG4 are suitable for preparation of immunoglobulin-fusion proteins. Ig fusion proteins are described for example in EP 314 317 A1 (Genentech) or EP 0 325 224 A2 (Zymogenetics Inc.).

5. As "active fractions" of a GH, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to GH.

6. GH to be formulated in accordance with the present invention may be used for treatment and/or prevention of a number of diseases or disorders, either alone or in combination with other active components. Such diseases or disorders are preferably related to insufficient endogenous GH production. Purified GH may be used e.g. for treatment and/or prevention GH deficiency, AIDS wasting, lipodystrophy (also called HARS—HIV-associated dysmorphia/dysmetabolic syndrome), or short bowel syndrome, in particular pediatric. Further diseases in which administration of growth homone may be indicated include liver cirrhosis, adult growth deficiency, atherosclerosis, Crohn's disease and Ulcerative Colitis, osteoarthritis, cardiac cachexia, congestive Heart Failure, chronic renal insufficiency, blood cell reconstitution or mobilization, male infertility, hematopoietic stem cell mobilization, multiple sclerosis, stroke, Multiple System Atrophy, or cancer.

The term "microcapsules" as used herein are micron- and submicron-scale particles, which have a structure comprising at least one inner solid core and an outer shell, and exhibiting a more or less spherical shape. Particles referred to as nanocapsules, which are particles in the submicron-scale range having the same structure as defined, are clearly encompassed by "microcapsules" as used herein. Typically, the weight-average diameter of the microcapsules of the invention ranges from approximately 100 nm to approximately 500 µm. More preferably, the average particle diameter is between about 1 µm about 100 µm. In another embodiment, the average diameter of the microspheres is between about 10 µm and about 80 µm, which is a very useful size range to be applied via a syringe equipped with a needle having a small diameter. The microcapsules of the present invention are very useful to achieve local tissue retention after intramuscular or subcutaneous injection so that a depot can be built up providing sustained release of the growth hormone incorporated into the particles.

The bulking agent employed in the particles according to the invention is preferably a sugar alcohol, a sugar, a sugar alcohol and/or an amino sugar. If the bulking agent is a sugar, it is preferably a mono-, di- or trisaccharide. Examples of monosaccharides that may be mentioned are glucose, mannose, galactose, fructose and sorbose; examples of disaccharides that may be mentioned are sucrose, lactose, maltose and trehalose, and an example of a trisaccharide that may be mentioned is raffinose. Preference is given to sucrose, lactose, maltose and trehalose, particularly preferred is sucrose.

Sugar alcohols are meant to be monosaccharides whose reactive carbonyl group has been reduced to the alcohol group, such as, for example, hexitols or pentitols. Sugar alcohols that can be used as bulking agents preferably comprises hexitols, such as, for example, mannitol, sorbitol, dulcitol, xylitol or ribitol. Particular preference is given to the presence of mannitol and/or sorbitol, very particularly preferred is mannitol.

Amino sugars, which can be used as bulking agents, are monosaccharides which contain a primary, secondary or tertiary amino group or an acylated amino group (—NH—CO—R) instead of a hydroxyl group. For the purposes of the invention, particular preference is given here to glucosamine, N-methylglucosamine, galactosamine and neuraminic acid.

The microparticles constituting the cores of the microcapsules can contain one bulking agent or a mixture of different bulking agents. If a mixture is used, such mixture can contain bulking agents from same group as, for example, from sugars, sugar alcohols or amino sugars or it can contain bulking agents of different groups as, for example, sugars together with sugar alcohols. The bulking agents are present in the microparticles constituting the cores of the microcapsules according to the invention in a proportion of from 20 to 99% of total weight, preferably from 30 to 90% of total weight, particularly preferably from 35 to 75% of total weight.

Surfactants which can be employed are all surfactants usually used in pharmaceutical preparations. Preferably the surfactants are non-ionic surfactants, particular preferably polyoxyethylene sorbitan fatty acid esters (polysorbates) and polyoxyethylene-polyoxypropylene block copolymers. The microparticles constituting the cores of the microcapsules can contain one or more surfactants. The surfactant or mixture of surfactants is present in such microparticles in a portion of from 0.01 to 2% of total weight, preferably from 0.05 to 0.5% of total weight, more preferable about 0.1% of total weight. Polyoxyethylene sorbitan fatty acid esters are also known as Polysorbate and under the trade name Tween®. Suitable polyoxyethylene sorbitan fatty acid esters are, in particular, polyoxyethylene (20) sorbitan monolaurate, polyoxyethylene (20) sorbitan monopalmitate and polyoxyethylene (20) sorbitan monostearate. Preference is given to polyoxyethylene (20) sorbitan monolaurate and polyoxyethylene (20) sorbitan monooleate, particular preference being given to polyoxyethylene (20) sorbitan monooleate. Polyoxyethylene-polyoxypropylene block copolymers are also known under the name Poloxamer. A particularly preferred polyoxyethylene-polyoxypropylene block copolymer is Poloxamer 188, commercialized under the trade name Lutrol® F68.

The lipids employed in the shell of the preparation according to the invention can be pure or blends of fatty alcohols, fatty acid esters and/or polyol esters wherein the polyol may be glycerol or a polyethylene glycol. In a particular mode of the invention, lipids are chosen among the group of phospholipids, mono-, di, and tri-glycerides of $C_8$-$C_{22}$ fatty acids, fatty acid esters, fatty alcohols, glycoglycerolipids, (which compounds contain one or two sugars linked glycosidically to glycerol or diacylglycerol), sucrose esters and their blends. The lipid employed preferably has a melting point of above the temperature of the human or animal body to be applied to in order to avoid fast delivery of the protein due to melting of the lipid. Preferably the lipid employed has a melting point of at least about 40° C., preferably in the range from 45° C. to 80° C., and more preferably in the range from 48° C. to 75° C.

In a preferred mode of the invention, the phospholipids used to form the shell are chosen among the group composed of phosphatidylcholin, phosphatidylglycerol, diphosphatidylglycerol, dipalmitoyl-phosphatidylcholine, dioleylphosphatidylethanolamine, dioleylphosphatidylcholin, dimyristol-phosphatidylglycerol, and their blends.

Esters of glycerol and fatty acids can be monoesters, diesters and/or triesters of glycerol and medium and/or long chain ($C_8$ to $C_{22}$) fatty acids and/or mixtures thereof. In a preferred mode of the invention, the mono-, di-, tri-glycerides are chosen among the group of mono-, di-, tri-glycerides of $C_8$-$C_{22}$ fatty acids, particularly among the group of mono-, di-, tri-glycerides of capric, caprylic, lauric, myristic, palmitic, stearic acids and their blends. Pure triglycerides, such as theories commercialised under the trade mark Dynasan®, for instance Dynasan® 114 (trimyristin), Dynasan® 118 (tristearin) can also be used to form the shell of the microcapsules. Hydrogenated vegetable oils can also be particularly suitable to be part of the lipid shell, preferably long chain hydrogenated vegetable oils of type I, such as palm oil, soybean oil or cottonseed oil. A particularly preferred hydrogenated vegetable oil is hydrogenated palm oil, such as commercialized under the trademark Dynasan® P 60.

The fatty acid esters are mono-esters of fatty acids and a mono- or divalent alcohol. Fatty acid esters that can be used in the present invention are preferably chosen from esters of $C_{12}$-$C_{22}$ acids with $C_1$-$C_{10}$ linear or branched aliphatic alcohols and their mixtures, such as ethyl palmitate, ethyl myristate, isopropyl myristate, ethyl stearate, octyl stearate and their mixtures. The fatty alcohols that can be used in the present invention are long chain ($C_{12}$-$C_{22}$) alcohols and their mixtures, such as cetyl alcohol, myristyl alcohol, cetearyl alcohol, stearyl alcohol, behenyl alcohol and their mixtures.

Examples of the glycoglycerolipids that can be used in the present invention are monogalactosyl diacylglycerol (MGDG) and digalactosyl diacylglycerol (DGDG), their mixtures and their acylated and sulfonated derivatives.

An example usable in the present invention is an ester of glycerol with behenic acid ($C_{22}$) (INCI: tribehenin, USP: glyceryl behenate), which is also marketed under the trademark Compritol® 888. It consists of mono- (12-18%), di- (52%) and tri-glycerides (28-32%) and, beside behenic acid (>85%), further contains $C_{16}$-$C_{20}$ fatty acids. Glyceryl behenate has a melting point between 69 and 74° C.

A further example for an ester of glycerol and fatty acids usable in the present invention is a lipid marketed under the trademark Precirol® ATO 5 (Precirol), which is a mixture of esters of glycerol with palmitic acid and stearic acid (glyceryl palmitostearate) and consists of mono- (8-17%), di- (54%) and tri-glycerides (29-38%) with palmatic acid and stearic acid. Precirol® ATO 5 has a melting point between 50 and 60° C. and a HLB value of about 2.

Esters of polyethylene glycol and fatty acids also known as polyglycolized glycerides and can be prepared by alcoholysis reaction of natural oils with polyethylene glycols (PEG). They are mixtures of monoesters, diesters and/or triesters of glycerides of long chain ($C_{12}$ to $C_{18}$) fatty acids, and PEG (mono- and/or di-) esters of long chain ($C_{12}$ to $C_{18}$) fatty acids and can include free PEG.

Polyglycolysed glycerides are, for example, commercially available from Gattefosse under the trademark GELUCIRE®. Usually the lipid marketed under GELUCIRE® trade mark is further specified by two double-digit numbers indicating their melting point and HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. Examples of polyglycolysed glycerides, which are present in the shell of the microcapsules are GELUCIRE® 50/13, GELUCIRE® 53/10 and preferably GELUCIRE® 50/02.

The shell of the particulate formulation can contain one lipid or a mixture of different lipids. If a mixture is used, such mixture can contain lipids from same group as, for example, from esters of glycerol and fatty acids or polyglycolysed glycerides or it can contain lipids of different groups as, for example, esters of glycerol and fatty acids together with polyglycolysed glycerides.

According to a preferred embodiment of the invention the lipid being present in the shell of microcapsules is a polyglycolyzed glyceride and/or an ester of glycerol and fatty acids.

Beside the lipid the shell can contain additives such as plasticizers, which may improve the film-forming ability of the lipid. Plasticizers are substances, which dissolve within the lipid and thereby increase the plasticity and fluidity of the lipid and usually are liquid at room temperature. The addition of plasticizers limitatess the formation of crystalline domains in the coating and reduces the porosity of the (lipid) coating material. Accordingly, one preferred embodiment of the present invention is directed to microcapsules, wherein the outer shell also contains a plasticizer.

The lipid or mixture of lipids together with additives, which may be present within the shell of the microcapsules such as plasticizers and dispersing agents, are referred within the present application to as "lipid phase".

Plasticizers which may be present in the lipid phase are, for example, lipids having a significantly lower melting point compared to the lipid used as coating material as, for example, medium-chain triglycerides (MCT) or amphiphilic block polyoxyethylene-polypropylene glycol copolymers (Poloxamers), such as Lutrol® F127. Their concentration with respect to the total weight of the lipid phase is in the range from 0 to 10%, preferably in the range from 1 to 6%.

The shell may also contain one or more dispersing agents facilitating the dispersion of the core hGH microparticles in the melted lipid. Accordingly, a further preferred embodiment is directed to microcapsules, wherein the lipid phase constituting the outer shell contains a dispersing agent for the inner core.

According to a particular preferred embodiment the dispersing agent is a phospholipid or a derivative thereof, for example soybean lecithins, preferably soybean lecithin. Their concentration with respect to the total weight of the whole shell-forming lipid phase is in the range from 0 to 2%, preferably in the range from 0.1 to 1%.

The microcapsules of the present invention can be manufactured by a two-step procedure. In the first step particles constituting the inner cores of the microcapsules are provided, which, in the second step are provided with an outer shell.

Preferably the first step in the manufacture of microcapsules is performed by using spray-drying technique and the second step is performed by using a process utilizing a fluid pressurized at a pressure close to its critical pressure ($P_c$). The expression "fluid pressurized at a pressure close to its critical pressure $P_c$" designates a fluid pressurized at a pressure comprised between 0.4 $P_c$ and 3 $P_c$. Accordingly, a further object of the present invention is directed to the process for preparing the microcapsules of the present invention, wherein the inner core is prepared by using a spray-drying technique and the outer shell is prepared by using a pressurized fluid-based process. According to a preferred embodiment, the process is operated at supercritical (SC) pressure. The expression "fluid at SC pressure" designates a fluid pressurized at a pressure higher than its critical pressure ($P_c$), whatever its temperature. It means that the temperature can be chosen lower or higher than the critical temperature ($T_c$). In a preferred mode of the invention, a microencapsulation process utilizing a Super-Critical Fluid (SCF) is used, which means that both pressure and temperature of the fluid will be higher than $P_c$ and $T_c$, respectively, at least in one part of the process.

As already mentioned the first step, i.e. the manufacture of the particles constituting the inner cores can be performed by using spray-drying technique. Spray-drying is, in principle, a solvent extraction process. The constituents of the product to be obtained are dissolved/dispersed in a liquid and then fed, for example by using a peristaltic pump, to an atomiser of a spray-dryer. A suitable atomizer, which can be used for atomization of the liquid, include nozzles or rotary discs. With nozzles, atomization occurs due to the action of the compressed gas, while in case of using rotary discs atomization occurs due to the rapid rotation of the disc. In both cases, atomization leads to disruption of the liquid into small droplets into the drying chamber, wherein the solvent is extracted from the aerosol droplets and is discharged out, for example through an exhaust tube to a solvent trap.

Suitable spray-drying techniques which can be used for preparation of the particles are well known and described, for example, by K. Masters in "Spray-drying Handbook", John Wiley & Sons, New York, 1984. In a preferred embodiment, atomization of the liquid is performed by using a nozzle. Examples of suitable spray-driers include lab scale spray-dryers from Buchi, such as the Mini Spray Dryer 290, or a MOBILE MINOR™, r a Pharma Spray Dryer PHARMASD® from Niro.

The spray-drying conditions have a major impact on product properties, moisture, particle size, morphology and the extent of protein aggregation and degradation. Temperature is the most important process parameter, since the exposure of proteins to high temperature could cause degradation. For the spray-dryer, two temperatures have to be controlled: inlet temperature and outlet temperature. The former is an independent process parameter and it can be set by the operator, the latter is dependent on the liquid feed rate, the atomizing air volumetric flow rate, the drying volumetric flow rate, and obviously the inlet temperature chosen.

According to an appropriate embodiment of the invention the inlet temperature is in the range from 90° C. to 150° C., preferably at from 95° C. to 130° C., and more preferably at from 100° C. to 120° C.

In accordance with the invention, the protein-, bulking agent- and surfactant-containing solutions used for the manufacture of the cores of the particulate formulation preparation comprises a surfactant in an amount from 0.001 to 2% by weight, preferably from 0.05 to 1% by weight and particularly preferably from 0.1% to 0.2% by weight. The solutions/dispersions used for spray-drying contain all ingredients being present in the inner core of the microcapsules, i.e. a growth hormone, a bulking agent and a surfactant. The solution/dispersion may contain further auxiliaries, for example for improving the stability of the growth hormone within such solution/dispersion or for improvement of its processability. For example the solution/dispersion can contain a buffer, as, for example, a phosphate buffer, citrate buffer, acetate buffer and/or succinate buffer. Such buffers can be present in a concentration from 1 mM to 100 mM, preferably from 5 mM to 50 mM, more preferably from 10 mM to 20 mM.

Preferably the solution/dispersion has a pH in the range from pH 5.0 to pH 8.5, preferably from pH 5.5 to pH 7.5, more preferably from pH 5.85 to pH 7.4. Specific duty preferred pH values are pH 5.85 and pH 7.4.

According to an appropriate embodiment of the growth hormone is present in a concentration from about 1 mg/ml to about 10 mg/ml.

According to a further embodiment, the solution/dispersion for spray-drying, comprises the bulking agent in a concentration from 1 mg/ml to 20 mg/ml, preferably from 2 mg/ml to 10 mg/ml, more preferably 5 mg/ml.

The shell containing at least one lipid can be applied to the protein-loaded cores by using a process where the core microparticles are put in contact with a fluid pressurized at a pressure P close to $P_c$, at a temperature close to $T_c$, so that it is able to swell the shell material. The expression "temperature close to $T_c$" designates a fluid at a temperature T in Kelvin (K) comprised between 0.8 $T_c$ (expressed in K) and 1.5 $T_c$ (expressed in K). For instance, this can be an encapsulation process as described in U.S. Pat. No. 5,057,342 (H. F. Bok et al., 1989), U.S. Pat. No. 5,066,522 (T. A. Cole et al., 1989), and also more recently in US 2003/0157183 A1. Such process consists in dissolving a pressurized fluid, in the melted lipid containing the dispersed core microparticles, leading to a so-called gas-saturated suspension that is further expanded through a nozzle to form solid lipid microcapsules containing the protein-loaded cores. The pressurized fluid is preferably chosen in the group comprised of nitrous oxide, propane, ethane and carbon dioxide ($CO_2$) used alone or in presence of co-solvents. $CO_2$ is the preferred pressurized fluid used in the invention. Co-solvents can be used to favor the dissolution of the pressurized fluid in the lipid phase and reduce the viscosity of the dispersion. Co-solvents used in the invention can be ketones, alcohols, esters, and light hydrocarbons bearing 3 to 8 carbon atoms, and preferably acetone, ethanol, n-propanol, isopropanol or ethyl acetate. They are used in a small concentration, lower than 10%, and preferably close to about 1%. The co-solvent is eliminated from the final microcapsules during the final depressurization/expansion phase of the process. Contrary to the process described in EP 0784 506 B, the lipid phase used in the present invention does not need to be solubilized in a supercritical fluid to implement the process. This is a key advantage of the present invention compared to EP 0784 506 B, which considerably widens the range of solid lipids usable to form the shell, leads to a much higher production yield, and guarantees a well-defined solid lipid shell of the same composition as the one of the original material introduced in the formulation. In a preferred embodiment of the present invention, the value of the fluid pressure P is in the range from about 0.75 $P_c$ to about 1.5 $P_c$, during the dispersion phase of the hGH core microparticles in the lipid melt. Accordingly, one preferred object of the invention is a process for preparing microcapsules, wherein the inner core is prepared by using spray-drying technique and the outer shell is prepared by using a fluid pressurized at a pressure comprised between 0.5 $P_c$ and 2 $P_c$, more preferably in the range from about 0.75 $P_c$ to about 1.5 $P_c$, $P_c$ being the critical pressure of the fluid.

In the encapsulation process of the present invention, the growth hormone-loaded core microparticles and the lipid agent are contacted with pressurized fluid, such as carbon dioxide ($CO_2$) leading to a suspension of the protein particles in melted, gas-saturated lipid agent(s). If $CO_2$ is used as the pressurized fluid, the pressure used during this phase is preferably chosen from the range from 5 MPa to 15 MPa, preferably from 5.8 MPa to 11.0 MPa. The pressurized fluid dissolution in the excipient generally induces excipient swelling/melting at a temperature much below (~10 to 50° C.) its melting/glass transition temperature, producing a saturated melt with a decreased viscosity.

The temperature of the saturated melt is preferably in the range from 30° C. to 70° C., more preferably from 35° C. to 65° C.

After homogeneous dispersion of the protein-loaded core microparticles in the melted lipid swollen by the pressurized fluid, depressurization of the saturated suspension through a nozzle leads to a large volume expansion of the fluid dissolved in the drops, breaking them up in small droplets that rapidly solidify because of the strong temperature decrease associated with the fluid expansion (i.e. the so-called Joule-Thomson effect). The fluid dissolution in the lipid, the dispersion and the depressurization conditions are adjusted in order to generate microcapsules with a quasi spherical morphology, a low porosity and high cohesion, leading to a low burst release. The pressure at which the homogeneous dispersion is depressurized is preferably in the range from ambient pressure to 5.5 MPa, more preferably from 1.5 MPa to 3.5 MPa, and most preferably at about 3 MPa.

According to a preferred embodiment the microcapsules of the present invention are prepared by a process comprising the steps
 (a) preparing an aqueous solution/dispersion comprising at least a growth hormone, a bulking agent and a surfactant;
 (b) spray-drying the aqueous solution/dispersion prepared in step (a) to produce protein-containing microparticles;
 (c) collecting the microparticles obtained in step (b);
 (d) preparing a homogeneous dispersion comprising the microparticles obtained in step (c) and the lipid in a pressurized fluid, under pressure and temperature conditions where the pressurized fluid is dissolved in the lipid phase;
 (e) depressurizing the dispersion prepared in step (d) through a nozzle and collecting the microcapsules obtained in step (e).

In a most preferred embodiment of the invention, the pressurized fluid used to implement the process is $CO_2$; the pressure for fluid dissolution and dispersion of hGH microparticles is about 6 MPa or 100 MPa, the temperature is in the range from about 60° C. to about 70° C., and the post-expansion pressure (that is the pressure in the depressurisation vessel) is in the range from about 3.0 MPa to about 5.0 MPa.

The microcapsules of the present invention can be administrated to a person in need thereof after suspension in a suitable pharmaceutically acceptable, injectable medium, for example via a needle having a small diameter and using a conventional syringe (25-30 Gauge). Preferably the suspension medium is an aqueous medium, which may further contain a suitable surfactant and/or a bulking agent. The term "aqueous" as used herein is understood as water or mixtures of water with other solvents, especially organic solvents. Aqueous solutions/suspensions are present if one or more component is dissolved or suspended in water or mixtures of a water with other solvents. If the aqueous solution/suspension contains one or more pharmacological active ingredient and such solution/suspension is suitable for therapeutic or prophylactic treatment of a man or an animal, such solution/suspension is a pharmaceutical preparation. If an organic solvent is present in the aqueous solution/suspension or pharmaceutical preparation, preferably such organic solvents are present which are suitable for parenteral administration such as dimethyl sulfoxide (DMSO), but preferably alcohols such as for example ethanol, 1,2-propanediol, glycerol, polyethylene glycols and glycofurol.

In order to increase the tolerability of parenteral administration, the osmolality of the suspension is preferably in the isotonic range, i.e. at an osmolality of from about 250 to 350 mOsmol/kg. The preparation can then be administered directly intravenously, intraarterially and also subcutaneously substantially without pain.

In order to achieve osmolality the aqueous medium may contain an isotonicity modifier, preferably a physiologically tolerated salt, such as, for example, sodium chloride or potassium chloride, or a physiologically tolerated polyol, such as, for example, glucose or glycerol, in a concentration necessary for isotonicity modification. In a preferred embodiment of the present invention the aqueous dispersion medium for the microcapsules is physiologic saline.

The dispersion medium may contain further auxiliaries such as suitable surfactants (POLOXAMER 188 and 407, SOLUTOL® HS 15, TWEEN® 20) and/or suitable sugar alcohols as, for example, mannitol and/or sorbitol. Alternatively, the suspension medium for administration of the microcapsules can be a non aqueous, injectable liquid of low viscosity, such as mixtures of medium chain triglycerides (fatty acid esters of glycerol). Preferred medium chain triglycerides are MYGLIOL® 812 (from Dynamit Nobel company), LABRAFAC® WL1349 (caprylic acid triglyceride from Gattefossé company, France), or LIPOID MCT (from Lipoid company, Germany).

In order to make the microcapsules suitable for parenteral administration available for application they are advantageously presented in the form, wherein they are hermetically closed in a sterile condition within a container suited for storage before use. Accordingly, a advantageous object of the present invention is a form of presentation of the microcapsules hermetically closed in a sterile condition within a container suited for storage before use. The elements used for providing a suspension of the microcapsules suitable for parenteral administration can advantageously be put together in a kit.

Accordingly, a further object of the present invention is a kit comprising a container containing the microcapsules comprising (1) an inner core comprising a growth hormone, a bulking agent, a surfactant and (2) an outer shell comprising at least one lipid and a container with dispersion medium. Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Unless explicitly stated otherwise all percent (%) data disclosed in this patent application are intended to mean percent by weight (% (w/w)).

The working examples explain the invention without being restricted thereto.

Spray-Drying

A Mini Spray Drier from Büchi was used. The hot gas was dehumidified air or nitrogen. The gas temperature ranged from about 80° C. to about 150° C.

Particle Size Distribution Analysis

Particle size distribution of powders prepared using the spray-drying method was characterized by Laser Diffraction System (Mastersizer 2000, Malvern Instruments) and by particle image analyser (Morphologi G2, Malvern Instruments). Mastersizer 2000 was used to measure the particle size distribution of the spray-dried powder in a liquid suspension using isopropanol as solvent. Each suspension was sonicated for about 2 min, before being loaded into the sample cell.

Deviant from this general procedure particle size of batch references DM5, GP5 b, D5 and DM10 was measured after resuspension in an aqueous solution containing Tween 20, whereby each suspension had been mixed with a vortex mixer (10 s) and sonicated for about 5 minutes.

Alternatively, powder was examined by optical microspcopy using Morphologi G2 (Malvern) to determine particle morphology and particle size distribution using the circular equivalent diameter. Particle size results are expressed in micrometers as number average distribution and parameters (D(n 0.9), D(n, 0.5) and D(n, 0.1), meaning that 90, 50 and 10% of the particle sample number is below the corresponding D value) and as Volume Distribution and parameters (D(v, 0.9), D(v, 0.5) and D(v, 0.1), meaning that 90, 50 and 10% of the particle sample volume is below the corresponding D value).

Protein Physico Chemical Characterisation—Size Exclusion and Reverse Phase Chromatography Samples of GH core microparticles obtained by spray-drying were analysed by size exclusion chromatography (SEC) (for the determination of protein content and of percentage aggregation) and by Reversed Phase High Performance Liquid Chromatography (RP-HPLC) (for the determination of % oxidized and deamidated forms). For RP-HPLC, the main GH chemical degradation products (oxidised and deamidated forms) were separated from the native form using a C4 column held at 45° C. Protein peaks were monitored at 220 nm.

Protein was eluted from the column by isocratic elution with a solvent composed of 71%50 mM Tris buffer and 29% isopropanol. The SEC analysis was conducted with a TSK gel G2000 SWXL column held at room temperature. Protein peaks were monitored at 214 nm. Protein was eluted from the column by isocratic elution with a solvent composed of 97% v/v 63 mM Phosphate buffer and 3% v/v isopropanol.

EXAMPLE 1

Screening and Selection of Suitable Operating Conditions for Atomization

Inlet Temperature (° C.)

Thermal stresses and mechanical stresses to which the protein is exposed to during spray-drying are well known to cause protein degradation. Operating conditions applied during spray-drying were optimised to retain protein stability during the spray-drying process. The inlet temperature and protein concentration in the feed material were varied to assess the effect on recovery of GH and level of degradation products in the microparticles produced. Several powders were obtained starting from two concentrations (20 mg/mL and 10 mg/mL) and setting different inlet temperatures (80° C., 90° C., 120° C. and 150° C.). For analysis, the powders were dissolved in phosphate buffered saline (PBS) pH 7.4 (to a theoretical concentration of 1 mg/mL) and analysed by SE-HPLC to assay the amount of hGH and the presence of high molecular weight substances (HMWS) in the powder.

In Table 1, are summarised the results for recovery and integrity of hGH by SEC-HPLC.

TABLE 1

SEC-HPLC results obtained from spray-dried powders

| hGH bulk | T inlet (Set) | T° C. outlet (Measured) | hGH recovery by SE-HPLC % | HMWS by SE-HPLC % | % moisture |
|---|---|---|---|---|---|
| 20 mg/mL | 80° C. | 35° C. | nt | nt | nt |
| 20 mg/mL | 90° C. | 45° C. | 32 | 0.68 | 2.2 |
| 20 mg/mL | 120° C. | 65° C. | 36 | 0.59 | 1.5 |
| 20 mg/mL | 150° C. | 100° C. | 30 | 1.14 | 0.5 |
| 10 mg/mL | 90° C. | 45° C. | 29 | 0.80 | 2.2 |
| 10 mg/mL | 120° C. | 65° C. | 36 | 0.80 | 1.1 |
| 10 mg/mL | 150° C. | 100° C. | 27 | 1.50 | 0.6 |

According to results shown in Table 1, spray-drying of the pure protein can have a deep impact on protein stability if protective agents are not utilised. Less than 40% hGH is recovered after spray-drying, regardless of the hGH concentration in the feed and the inlet temperature used. This low recovery can be related to the formation of large insoluble aggregates, that are visible as residual white particles after reconstitution.

A greater percentage of hGH HMWS was determined for powders produced at a higher inlet temperature, confirming the risk of heat-induced degradation caused by the exposure of the protein to high temperatures. Use of higher inlet temperatures might also favour production of microparticles with a lower moisture content (Table 1). However, a moisture content up to 7-10% obtained for these core microparticles with a lower inlet temperature is acceptable, and consistent with a good stability of the protein.

EXAMPLE 2

Investigation into the Effects of Bulking Agents and Surfactants

In order to investigate the capability of excipients to prevent degradation of hGH during spray-drying, several solutions containing sugars (trehalose, sucrose, mannitol at 10 mg/mL) with or without the addition of surfactant (Polysorbate 20 and Poloxamer 188 at 0.1%) were prepared for spray-drying. The hGH concentration was set at 2 mg/mL. The solutions were prepared by dissolving the surfactant and the bulking agent in Phosphate buffer at pH 7.4 then adding the hGH bulk under gentle mixing. The solutions were atomized at an inlet temperature of 120° C. an air flow rate of 538 L/h a solution flow rate of 5 mL/min and aspirator speed of 38 m$^3$/h. The powder samples were assayed for hGH recovery and purity (by SE-HPLC) and characterized as regards particle size distribution (by Mastersizer 2000). Formulations containing surfactants were also analysed for % increase in oxidized and dearnidated forms (by RP-HPLC), compared to non spray-dried reference hGH material. The compositions used for spray-drying and the analytical data (recovery and % HMW (by SE-HPLC)) of the formulations obtained are summarized in Table 2. For analysis, the powders were dissolved in PBS pH 7.4 (to a theoretical concentration of 1 mg/mL) and assayed by SE-HPLC for hGH recovery and integrity.

TABLE 2

Physico-chemical characterisation of hGH microparticles obtained by spray-drying as a function of bulking agents (carbohydrates) concentration and surfactant type and concentration.

| Bulking agent | Conc. Bulking agent (mg/mL) | Polysorbate 20 (w/w %) | Poloxamer 188 (w/w %) | Protein Recovery % | HMWS % | Increase in oxidized and deamidated forms by RP-HPLC (%)* |
|---|---|---|---|---|---|---|
| Trehalose | 2 | — | 0.1 | 97 | 2.7 | 2 |
| Trehalose | 5 | — | — | 47 | 0.80 | |
| Trehalose | 10 | — | — | 43 | 1.26 | |
| Trehalose | 10 | 0.1 | — | 97 | 4.7 | 0 |
| Trehalose | 10 | — | 0.1 | 97 | 3 | 0 |
| Trehalose | 20 | — | — | 43 | 0.36 | — |
| Sucrose | 2 | 0.1 | — | 97 | 3.3 | 0 |
| Sucrose | 2 | — | 0.1 | 98.3 | 1.7 | 0 |
| Sucose | 10 | — | — | 20 | 0.03 | |
| Sucose | 10 | 0.1 | — | 90 | 10.7 | 0 |
| Sucrose | 10 | — | 0.1 | 98 | 2.8 | 0 |
| Mannitol | 10 | 0.1 | — | 94 | 9 | 3.22 |

TABLE 2-continued

Physico-chemical characterisation of hGH microparticles obtained by spray-drying as a function of bulking agents (carbohydrates) concentration and surfactant type and concentration.

| Bulking agent | Conc. Bulking agent (mg/mL) | Polysorbate 20 (w/w %) | Poloxamer 188 (w/w %) | Protein Recovery % | HMWS % | Increase in oxidized and deamidated forms by RP-HPLC (%)* |
|---|---|---|---|---|---|---|
| Mannitol | 10 | — | 0.1 | 97 | 5.8 | |
| Mannitol | 10 | — | — | 44 | 0.64 | 0 |

When hGH is formulated with carbohydrates only, a low recovery (from 20% to 44%) is measured, regardless of the carbohydrate concentration. This can be related to the formation of large insoluble aggregates that are visible as white particles after reconstitution, and that are not present when a surfactant is used. The addition of Polysorbate 20 or Poloxamer 188 at 0.1% wt considerably improves the recovery regardless of type of surfactant, presumably by limiting interfacial exposure of the protein, and allows a total dissolution of powder before analysis.

hGH formulated with carbohydrates and surfactants was analysed also as regards % oxidized and deamidated forms by RP-HPLC. Powders were dissolved in PBS pH 7.4 to obtain a theoretical concentration of 2 mg/mL. In parallel, non-spray-dried hGH bulk was tested as a reference.

Results obtained, shown in Table 2, showed that the percent oxidized and deamidated forms of hGH did not increase for the atomized samples as compared to a reference non-spray-dried bulk.

EXAMPLE 3

Particle Size Distribution

The particle size of the powders described in Table 2 is shown in the Table 4: the diameters are expressed both as a volume distribution and a number distribution.

The mean diameter of the spray-dried particles is less than 5 μm when expressed as a number distribution indicating the atomized powder has a fine texture. The volume distribution showed a larger mean diameter, indicating large agglomerates are present in a very low percentage.

Coating of Microparticles Using a Pressurized Fluid Process

A SCF equipment as schematically represented in FIG. 1 was used. In all experiments, the following procedure was used:

The mixture particle/coating agent(s) (2) was placed in the mixing cell (1) and contacted with pressurized $CO_2$, pumped from a $CO_2$ tank (4) at mixing conditions during ten minutes.

The mixture was then agitated during one hour with a stirrer (3). During this step, pulverization conditions were settled in the collecting vessel (7) equipped with a back-pressure regulator (8).

After one hour, agitation was stopped and pulverization through the nozzle (6) was started by turning on the valve.

At the end of pulverization, the collecting vessel (7) was slowly depressurized; the sample was collected and sieved (500 μm).

Eight formulations of hGH-loaded lipid microparticles with a 5% w/w payload of microparticles in the lipid microcapsules were prepared by using this pressurized fluid-based encapsulation process and analytically characterized (hGH physico-chemical characterization, in vitro hGH release profile). In addition, a 10 wt % payload formulation was also prepared for preliminary process and analytical assessment. Process parameters and formulation data are summarized in Table 5.

Samples produced with a 5 wt % payload are acceptable in terms of particle size distribution, aspect and production yield. Furthermore, the preliminary formulation with a 10 wt % payload shows that producing particles with such a high payload, which is potentially necessary to achieve the target dose, seems feasible.

TABLE 4

Particle size distribution of spray-dried powder containing hGH

| | Number Distribution | | | Volume Distribution | | |
|---|---|---|---|---|---|---|
| FORMULATION | D(0.1) μm | D(0.5) μm | D(0.9) μm | D(0.1) μm | D(0.5) μm | D(0.9) μm |
| hGH 2 mg/mL + Sucrose 10 mg/mL + Polysorbate 20 0.1% | 1.09 | 1.74 | 3.46 | 6.01 | 28.24 | 66.69 |
| hGH 2 mg/mL + Sucrose 10 mg/mL + Poloxamer 188 0.1% | 0.54 | 0.86 | 3.86 | 3.69 | 8.18 | 8.56 |
| hGH 2 mg/mL + Trehalose 10 mg/mL + Polysorbate 20 0.1% | 1.54 | 2.37 | 4.08 | 2.95 | 6.55 | 49.95 |
| hGH 2 mg/mL + Trehalose 10 mg/mL + Poloxamer 188 0.1% | 0.54 | 0.78 | 4.00 | 9.10 | 49.22 | 160.74 |
| hGH 2 mg/mL + Mannitol 10 mg/mL + Polysorbate 20 0.1% | 0.76 | 1.21 | 2.90 | 1.63 | 5.32 | 12.01 |
| hGH 2 mg/mL + Mannitol 10 mg/mL + Poloxamer 188 0.1% | 0.61 | 0.88 | 1.74 | 1.65 | 6.70 | 15.62 |

TABLE 5 hGH-loaded lipid microcapsules; Process operating parameters and formulation composition (10 bar = 1.0 MPa)

| Batch reference | Pay-load | Coating agent | Additives | Pre-expansion Temperature/ Pressure | Post-expansion Pressure |
|---|---|---|---|---|---|
| 1P5 | 5% | PRECIROL ATO 5 | 0.5% Soybean lecithin | 60 bar/60° C. | 30 bar |
| 2P5 | 5% | PRECIROL ATO 5 | 0.5% Soybean lecithin | 60 bar/60° | 30 bar |
| 3P5 | 5% | PRECIROL ATO 5 | 0.5% Soybean lecithin 5% MCT (Miglyol) | 60 bar/60° C. | 30 bar |
| 4P5 | 5% | PRECIROL ATO 5 | 0.5% Soybean lecithin 2.5% Lutrol F127 | 60 bar/60° C. | 30 bar |
| 5P5 | 5% | PRECIROL ATO 5 | 0.5% Soybean Lecithin 2.5% Lutrol F127 | 60 bar/60° C. | 30 bar |
| 1G5 | 5% | GELUCIRE 50/02 | 0.5% Soybean lecithin | 100 bar/60° C. | 50 bar |
| 2G5 | 5% | GELUCIRE 50/02 | 0.5% Soybean lecithin | 100 bar/60° C. | 30 bar |
| 3G5 | 5% | GELUCIRE 50/02 | 0.5% Soybean lecithin | 100 bar/60° C. | 30 bar |
| 1GP5 | 5% | 50% GELUCIRE 50/02 50% PRECIROL ATO 5 | 0.5% Soybean lecithin | 100 bar/60° C. | 50 bar |
| 1G10 | 10% | GELUCIRE 50/02 | 0.5% Soybean lecithin | 100 bar/60° C. | 50 bar |
| DM5 | 5% | DYNASAN P60F | 5% MCT 0.5% Soybean lecithin | 110 bar/70° C. | 30 bar |
| GP5 b | 5% | GELUCIRE 50/02/ PRECIROL Ato 5 50/50 | 0.5% Soybean lecithin | 70 bar/60° C. | 30 bar |
| D5 | 5% | DYNASAN P60F | 0.5% Soybean lecithin | 110 bar/70° C. | 30 bar |
| DM10 | 10% | DYNASAN P60F | 5% MCT 0.5% Soybean lecithin | 110 bar/70° C. | 30 bar |

Analytical results are summarized in Table 6. hGH-loaded lipid microcapsules produced using this process showed a very high protein recovery (>98%) and almost no protein degradation induced by the process, since the increase in related protein degradation products (by RP-HPLC) remains lower than 6%.

TABLE 6 hGH-loaded lipid microcapsules; Analytical data

| Composition | Theoretical hGH content w/w (%) | SEC HPLC | | | RP HPLC* Related proteins | Moisture content (%) |
|---|---|---|---|---|---|---|
| | | Total hGH Content w/w (%) | Purity w/w (%) | HMWS w/w (%) | | |
| hGH microparticles* | 38 | 37.5 | 99.48 | 0.52 | 6.3 | 7-10 |
| hGH microparticles** | 38 | 32.34 | 99.44 | 0.56 | 6.5 | n.d. |
| hGH microparticles*** | 38 | 35.21 | 99.44 | 0.56 | 6.66 | 7.42 |
| 1P5 | 1.75 | 1.55 | 99.05 | 0.95 | 8.04 | 0.78 |
| 2P5 | 1.7 | 1.59 | 98.89 | 1.11 | 8.76 | 0.79 |
| 3P5 | 1.75 | 1.22 | 98.52 | 1.48 | 10.69 | 1.0 |
| 4P5 | 1.75 | 1.5 | 99.05 | 0.95 | 10.70 | 1.14 |
| 5P5 | 1.75 | 1.48 | 99.15 | 0.85 | 11.3 | 0.97 |
| 1G5 | 1.88 | 1.63 | 99.17 | 0.83 | 7.35 | 1.0 |
| 2G5 | 1.75 | 1.52 | 98.45 | 1.55 | 7.00 | 0.7 |
| 3G5 | 1.7 | 1.79 | 98.83 | 1.17 | 8.25 | 0.93 |
| 1GP5 | 1.7 | 1.72 | 99.04 | 0.96 | 8.12 | 0.62 |
| 1G10 | 3.4 | 3.26 | 99.35 | 0.65 | 7.43 | 1.3 |
| DM5 | 1.7 | 1.40 | 99.52 | 0.48 | 5.89 | 1.19 |
| GP5 b | 1.7 | 1.54 | 99.14 | 0.86 | 8.30 | 1.37 |
| D5 | 1.7 | 1.46 | 99.56 | 0.54 | 6.93 | 1.18 |
| DM10 | 3.4 | 2.85 | 99.14 | 0.86 | 5.69 | 0.6 |

*reference for batches 1G5, 1GP5, 1G10.
**reference for batches 1P5, 2P5, 3P5, 4P5.
***reference for batches 2G5, 3G5, 5P5.

TABLE 7

Production yield and Particle size distribution of hGH loaded microcapsules

| Composition | PSD (μm) d(0.1) | d(0.5) | d(0.9) | Yield (%) |
|---|---|---|---|---|
| 1P5 | 7.6 | 38.4 | 100.0 | 78 |
| 2P5 | 3.9 | 34.4 | 86.8 | 79 |
| 3P5 | 6.8 | 39.6 | 111.1 | 81 |
| 4P5 | 3.1 | 19.8 | 71.6 | 76 |
| 5P5 | 6.6 | 31.9 | 98.7 | 75 |
| 1G5 | 3.0 | 77.3 | 242.0 | 69 |
| 2G5 | 2.9 | 31.9 | 101.8 | 79 |
| 3G5 | 2.5 | 14.1 | 117.4 | 81 |
| 1GP5 | 2.8 | 27.8 | 161.6 | 82 |
| 1G10 | 1. | 4.5 | 14.6 | 63 |
| DM5 | 6.3 | 62.2 | 157.8 | N.A. |
| GP5 b | 3.6 | 34.7 | 100.1 | N.A. |
| D5 | 5.0 | 49.7 | 129.7 | N.A. |
| DM10 | 5.6 | 65.7 | 184.9 | N.A. |

In addition, the in vitro release characteristics of these formulations were also quantified. Results are presented for Gelucire®-based formulations in FIGS. 2a & 2b, Precirol®-based formulations in FIG. 3, and Precirol®/Gelucire®-based formulations in FIG. 4. Results for a further Precirol®/Gelucire®-based formulation as well as from Dynasan®-based formulations are presented in FIG. 6.

Gelucire®-based formulations exhibit a low in vitro burst release (around 20-30%) and a sustained-release profile. In vitro release profiles of two different batches of Gelucire® 50/02 formulations (1G5 and 3G5) are similar, and make it possible to conclude that the process is highly reproducible. Low burst release was also found with the formulation produced with 10 wt % payload of hGH microparticles.

It is remarkable that for the same hGH loading (5%) the in vitro burst is further reduced in the Dynasae-based formulations and that such low burst is combined with an improved sustained release profile.

For the same hGH loading (5%), the Precirol®-based formulations exhibited a higher burst, but then a slower release rate. In vitro release profiles of two different batches of Precirol® formulations (1P5 and 5P5) make it possible to conclude that the process is highly consistent.

It was further demonstrated that, starting from spray-dried micronized hGH particles, hGH-loaded injectable solid lipid microcapsules exhibiting a low in vitro burst release and a in vitro sustained-release profile can be produced using the pressurized fluid process. It was shown that these formulations can be produced without any hGH denaturation (low level of HMWS and increase in related protein-degradation products).

A study was conducted to assess the storage stability of hGH-loaded injectable lipid microcapsules, filled in 3 mL glass vials under nitrogen, at 2-8° C. and 25° C. The samples were analysed by SEC for determination of the protein content and the aggregation level of the protein and RP-HPLC analysis was carried out for the determination of the oxidized and deamidated forms. For the analysis, hGH was extracted from the lipid microparticles using dichloromethane. The solvent dissolves the lipid in the microparticles and precipitates the protein. The protein precipitate is washed with the solvent, dried, and then reconstituted with an aqueous phase prior to HPLC analysis. The chromatographic analyses were conducted as described above. The samples were also analysed for the moisture content by coulometric determination. Samples were extracted and analysed at initial, time 2 weeks, 1 month and 2 months. The results in Tables 8 and 9 show that hGH in lipid microparticles obtained by the process are stable at 2-8° C. and 25° C. at least over 2 months.

Those skilled in the art will recognize, or be able to ascertain using no more than routine experimentation, many equivalents to the specific embodiments of the invention described specifically herein. Such equivalents are intended to be encompassed in the scope of the following claims.

TABLE 8

Stability of hGH lipid microcapsules at 2-8° C.

| SAMPLE | Theoretical hGH content w/w (%) | SE-HPLC Total hGH content w/w (%) | Purity w/w (%) | HMWS w/w (%) | RP-HPLC Related proteins | Moisture content (%) |
|---|---|---|---|---|---|---|
| T zero ||||||| 
| 3G5 | 1.7 | 1.5 | 99.1 | 0.9 | 10.15 | 1.3 |
| 2P5 | 1.7 | 1.6 | 98.9 | 1.1 | 8.5 | 1.0 |
| 1GP5 | 1.7 | 1.7 | 99.1 | 0.9 | 9.5 | 0.8 |
| 1G10 | 3.4 | 3.2 | 99.0 | 1.0 | 8.0 | 1.1 |
| 2 weeks 2-8° C. |||||||
| 3G5 | 1.7 | 1.4 | 98.9 | 1.1 | 11.6 | 1.0 |
| 2P5 | 1.7 | 1.5 | 98.6 | 1.4 | 9.5 | 1.3 |
| 1GP5 | 1.7 | 1.6 | 98.8 | 1.3 | 9.5 | 1.2 |
| 1G10 | 3.4 | 3.1 | 98.8 | 1.2 | 8.0 | 2.8 |
| 1 Month 2-8° C. |||||||
| 3G5 | 1.7 | 1.5 | 99.0 | 1.0 | 9.9 | 0.8 |
| 2P5 | 1.7 | 1.8 | 98.8 | 1.2 | 9.2 | 1.0 |
| 1GP5 | 1.7 | 1.7 | 99.0 | 1.0 | 9.7 | 0.9 |
| 1G10 | 3.4 | 3.2 | 99.0 | 1.0 | 7.7 | 1.2 |
| 2 Months 2-8° C. |||||||
| 3G5 | 1.7 | 1.6 | 99.0 | 1.0 | 9.5 | 0.8 |
| 2P5 | 1.7 | 1.8 | 98.8 | 1.2 | 9.0 | 0.9 |

TABLE 8-continued

Stability of hGH lipid microcapsules at 2-8° C.

| | | SE-HPLC | | | | |
|---|---|---|---|---|---|---|
| SAMPLE | Theoretical hGH content w/w (%) | Total hGH content w/w (%) | Purity w/w (%) | HMWS w/w (%) | RP-HPLC Related proteins | Moisture content (%) |
| 1GP5 | 1.7 | 1.8 | 98.9 | 1.1 | 9.0 | 0.9 |
| 1G10 | 3.4 | 3.3 | 98.9 | 1.1 | 7.4 | 1.9 |

TABLE 9

Stability of hGH lipid microcapsules at 25° C.

| | | SE-HPLC | | | | |
|---|---|---|---|---|---|---|
| SAMPLE | Theoretical hGH content w/w (%) | Total hGH content w/w (%) | Purity w/w (%) | HMWS w/w (%) | RP-HPLC Related proteins | Moisture content (%) |
| T zero | | | | | | |
| 3G5 | 1.7 | 1.4 | 99.0 | 1.0 | nt | 1.3 |
| 2P5 | 1.7 | 1.8 | 98.8 | 1.2 | 9.8 | 0.9 |
| 1GP5 | 1.7 | 1.6 | 98.9 | 1.1 | 10.7 | 0.8 |
| 1G10 | 3.4 | 3.2 | 99.0 | 1.0 | 7.7 | 1.1 |
| 2 weeks 25° C. | | | | | | |
| 3G5 | 1.7 | 1.4 | 98.9 | 1.1 | 11.7 | 1.1 |
| 2P5 | 1.7 | 1.6 | 98.6 | 1.4 | 8.8 | 1.5 |
| 1GP5 | 1.7 | 1.5 | 98.8 | 1.2 | 11.0 | 1.2 |
| 1G10 | 3.4 | 3.2 | 98.8 | 1.3 | 9.2 | 1.8 |
| 1 Month 25° C. | | | | | | |
| 3G5 | 1.7 | 1.5 | 98.9 | 1.2 | 12.3 | 0.9 |
| 2P5 | 1.7 | 1.5 | 98.9 | 1.1 | 10.1 | 1.0 |
| 1GP5 | 1.7 | 1.7 | 98.5 | 1.5 | 10.5 | 0.9 |
| 1G10 | 3.4 | 3.3 | 98.8 | 1.2 | 8.7 | 1.3 |
| 2 Months 25° C. | | | | | | |
| 3G5 | 1.7 | 1.5 | 98.8 | 1.2 | 12.7 | 0.7 |
| 2P5 | 1.7 | 1.8 | 98.5 | 1.5 | 10.7 | 0.9 |
| 1GP5 | 1.7 | 1.7 | 98.7 | 1.3 | 12.2 | 1.0 |
| 1G10 | 3.4 | 3.4 | 98.7 | 1.3 | 9.3 | 1.3 |

BRIEF DESCRIPTION OF THE DRAWINGS

FIG. 2*a*: In vitro release profiles for 2 GELUCIRE®-based microcapsule formulations (1G5, 3G5), containing 5% hGH core microparticles.

FIG. 2*b*: In vitro release profiles for a GELUCIRE®-based microcapsule formulation with 10% payload hGH microparticles.

FIG. 3: In vitro release profiles for 2 PRECIROL®-based microcapsule formulations (1P5, 5P5).

FIG. 4: In vitro release profiles for one PRECIROL®/GELUCIRE®-based formulation (1GP5).

FIG. 5: Amino acid sequence of human growth hormone

FIG. 6: In vitro release profiles for microcapsule formulations (DMS, GP5b, D5, DM10).

Figure 1:
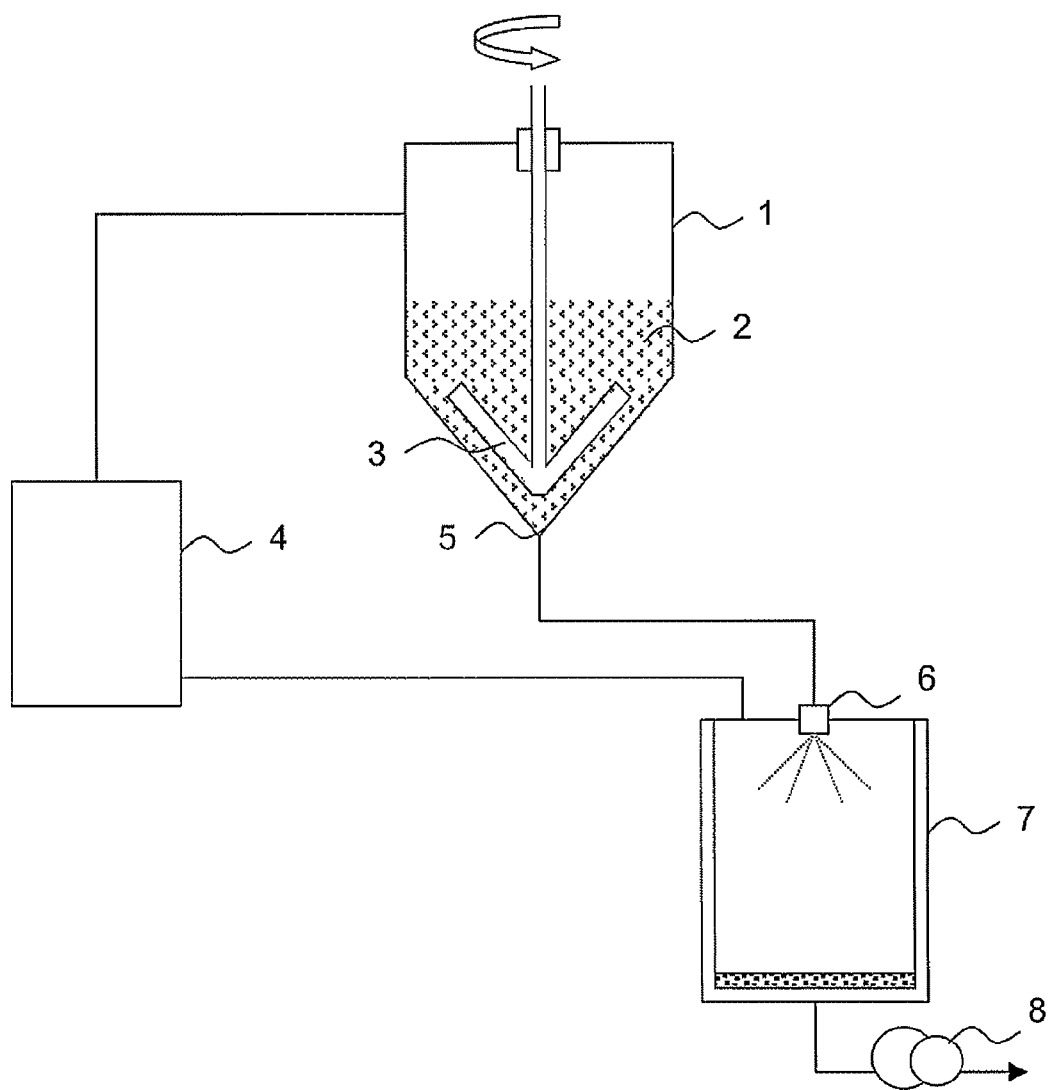
FIG. 1: SCF equipment as schematically represented.

We claim:

1. A microcapsule comprising
   (1) at least one inner solid core containing at least a growth hormone, a bulking agent which is a sugar alcohol, a sugar or an amino sugar, a surfactant which is a polysorbate or a polyoxyethylene-polyoxypropylene block copolymer; and
   (2) an outer shell comprising at least one lipid which comprises a phospholipid or a derivative thereof which is a dispersing agent for the inner solid core,
   wherein said microcapsule is produced by a process that yields over 98% growth hormone upon recovery, based on the theoretical content of said growth hormone.

2. A microcapsule according to claim 1, wherein the growth hormone is human growth hormone (hGH) or a functional derivative, fragment, variant, analogue, or a salt thereof which retains the biological activity of human growth hormone.

3. A microcapsule according to claim 1, wherein the sugar is a mono-, di- or trisaccharide.

4. A microcapsule according to claim 3, wherein the sugar is sucrose, lactose, maltose or trehalose.

5. A microcapsule according to claim 1, wherein the amino sugar is glucosamine, N methyl-glucosamine, galactosamine or neuraminic acid.

6. A microcapsule according to claim 1, wherein the sugar alcohol is mannitol, sorbitol, dulcitol, xylitol or ribitol.

7. A microcapsule according to claim 1, wherein the surfactant is the polyoxyethylene sorbitan fatty acid ester polyoxyethylene (20) sorbitan monooleate or polyoxyethylene (20) sorbitan monolaurate.

8. An isolated microcapsule according to claim 1, wherein the lipid has a melting point of at least about 40° C.

9. A microcapsule according to claim 1, wherein the lipid is a fatty alcohol, a fatty acid ester, a polyol ester, or an ester of at least one fatty acid and at least one polyol.

10. A microcapsule according to claim 1, wherein the lipid is a polyglycolyzed glyceride and/or an ester of glycerol and fatty acids.

11. A microcapsule according to claim 1, wherein the lipid is the polyglycolyzed glyceride Gelucire® 50/02, a glyceryl (palmitostearate), or a blend of them.

12. A microcapsule according to claim 1, wherein the outer shell also contains a plasticizer.

13. A microcapsule according to claim 12, wherein the plasticizer is a medium chain triglyceride of a Poloxamer.

14. A pharmaceutical formulation comprising a microcapsule according to claim 1 being suspended in a dispersion medium.

15. A microcapsule according to claim 1 hermetically closed in a sterile condition within a container suited for storage before use.

16. A kit comprising a container containing the microcapsules according to claim 1 comprising (1) an inner core comprising a growth hormone, a bulking agent, a surfactant and (2) an outer shell comprising at least one lipid which comprises a phospholipid or a derivative thereof which is a dispersing agent for the inner solid core, wherein said microcapsule is produced by a process that yields over 98% growth hormone upon recovery, based on the theoretical content of said growth hormone, and a container with dispersion medium.

17. A process for preparing a formulation according to claim 1 wherein the inner core of is prepared by using spray-drying technique and the outer shell is prepared by using pressurized fluid-based process.

18. A process for preparing microcapsules according to claim 17, comprising the steps
(a) preparing an aqueous solution/dispersion comprising at least a growth hormone, a bulking agent and a surfactant;
(b) spray-drying the aqueous solution/dispersion prepared in step (a) to produce protein-containing microparticles;
(c) collecting the microparticles obtained in step (b);
(d) preparing a homogeneous dispersion comprising the microparticles obtained in step (c) and the phase constituting the outer shell in a pressurized fluid, under pressure and temperature conditions where the pressurized fluid is dissolved in the lipid phase;
(e) depressurizing the dispersion prepared in step (d) through a nozzle and collecting the encapsulated protein particles obtained in step (e).

19. A process for preparing microcapsules according to claim 18, wherein the inner core of is prepared by using spray-drying technique and the outer shell is prepared by using a fluid pressurized whose pressure during the dissolution and dispersion step is comprised between 0.4 Pc and 3 Pc, preferably between 0.5 Pc and 2 Pc, more preferably between 0.75 Pc and 1.5 Pc, Pc being the critical pressure of the fluid.

20. A process for preparing microcapsules according to claim 18 wherein the pressurized fluid is carbon dioxide.

21. A process according to claim 20, wherein the carbon dioxide swells the lipid to form a saturated melt during the dissolution and dispersion step (d).

22. A process according to claim 20, wherein the temperature during the dissolution and dispersion step (d) is in the range from 30° C. to 70° C., preferably from 35° C. to 65° C., and more preferably at about 60° C.

23. A process according to claim 20, wherein the pressure during the dissolution and dispersion step (d) is in the range from 6.0 MPa to 11.0 MPa, preferably close to about 6 MPa or 10 MPa, and the post-expansion pressure is in the range from 1.0 MPa to 5.5 MPa, preferably in the range from 1.5 MPa to 3.5 MPa, and more preferably in the range from 3.0 MPa to 5.0 MPa.

24. A microcapsule according to claim 6, wherein the sugar alcohol is mannitol.

25. A microcapsule according to claim 1, wherein the dispersing agent is soybean lecithin.

26. A microcapsule according to claim 8, wherein the lipid has a melting point from 45° C. to 80° C.

27. A microcapsule according to claim 26, wherein the lipid has a melting point from 48° C. to 75° C.

* * * * *